United States Patent
Smothers

(10) Patent No.: US 9,863,899 B2
(45) Date of Patent: Jan. 9, 2018

(54) SYSTEM AND METHOD FOR MEASURE OPERATION BENEFITS OF FLIGHT DECK AVIONICS

(71) Applicant: CESSNA AIRCRAFT COMPANY, Wichita, KS (US)

(72) Inventor: Stephen William Smothers, Clearwater, KS (US)

(73) Assignee: Textron Innovations, Inc., Providence, RI (US)

( * ) Notice: Subject to any disclaimer, the term of this patent is extended or adjusted under 35 U.S.C. 154(b) by 163 days.

(21) Appl. No.: 14/989,938

(22) Filed: Jan. 7, 2016

(65) Prior Publication Data

US 2017/0200378 A1 Jul. 13, 2017

(51) Int. Cl.
| | |
|---|---|
| G08G 5/00 | (2006.01) |
| G01C 21/20 | (2006.01) |
| G06F 17/50 | (2006.01) |
| G01N 25/08 | (2006.01) |
| G01N 25/14 | (2006.01) |
| G01N 30/30 | (2006.01) |
| G01N 33/28 | (2006.01) |
| G01N 30/12 | (2006.01) |
| G01N 30/88 | (2006.01) |

(52) U.S. Cl.
CPC ............ *G01N 25/08* (2013.01); *G01N 25/14* (2013.01); *G01N 30/12* (2013.01); *G01N 30/30* (2013.01); *G01N 30/88* (2013.01); *G01N 33/2823* (2013.01); *G01N 2030/127* (2013.01); *G01N 2030/3076* (2013.01); *G01N 2030/8854* (2013.01)

(58) Field of Classification Search
CPC .. G08G 5/0043; G08G 5/0013; G05G 5/0021; G01C 21/20; G06F 17/5009
See application file for complete search history.

(56) References Cited

U.S. PATENT DOCUMENTS

| | | |
|---|---|---|
| 6,005,513 A | 12/1999 | Hardesty et al. |
| 6,134,500 A | 10/2000 | Tang et al. |
| 8,554,460 B2 | 10/2013 | Struzik |
| 2009/0125222 A1 | 5/2009 | McCullough et al. |
| 2010/0103022 A1* | 4/2010 | Stefani ................. G08G 5/0013 342/30 |

(Continued)

*Primary Examiner* — Dale Moyer
(74) *Attorney, Agent, or Firm* — Erise IP, P.A.

(57) ABSTRACT

Embodiments of the present disclosure relate to an Operational Flight Efficiency Evaluation (OFEE) system for an aircraft. The system comprises an Avionics Situation Awareness Device (ASAD). The ASAD includes one or more processors, a memory communicatively coupled to the one or more processors, and a flight data collection interface configured to, via the one or more processors, collect empirical flight data for a flight and store the empirical flight data in the memory. The OFEE also includes a Simulation And Comparison System (SACS) in communication with the ASAD. The ASAD includes a database communicatively coupled to a National Airspace System (NAS). The database is also configured to automatically acquire and store avionics systems available for flight efficiencies from the NAS. The ASAD also includes a simulator configured to identify at least one avionics upgrade based on the collected empirical flight data and the avionics systems available for flight efficiencies.

8 Claims, 5 Drawing Sheets

(56) References Cited

U.S. PATENT DOCUMENTS

| | | | |
|---|---|---|---|
| 2011/0202251 A1* | 8/2011 | Luppold | F02C 9/42 |
| | | | 701/100 |
| 2011/0208415 A1 | 8/2011 | Mere et al. | |
| 2012/0191332 A1* | 7/2012 | Sawhill | G08G 5/0013 |
| | | | 701/120 |
| 2013/0345956 A1 | 12/2013 | Struzik | |
| 2014/0013002 A1 | 1/2014 | Holstein et al. | |
| 2015/0324501 A1* | 11/2015 | Desell | G01C 23/00 |
| | | | 703/2 |
| 2016/0019795 A1* | 1/2016 | Chircop | G08G 5/0034 |
| | | | 701/7 |

* cited by examiner

SYSTEM AND METHOD FOR MEASURE OPERATION BENEFITS OF FLIGHT DECK AVIONICS

BACKGROUND

The Federal Aviation Administration (FAA) estimates that increasing congestion in the air transportation system of the United States, if unaddressed, would cost the American economy $22 billion annually in lost economic activity by 2022. In particular, the FAA estimates that such congestion would introduce significant inefficiencies in the air transportation system. Accordingly, in response to the concern of increasing congestion, the government, along with industry leaders, plans to implement a Next Generation Air Transportation System (NextGen) across the United States to address inefficiencies caused by the increasing congestion. In particular, NextGen is a system that is to be used to transform America's Air Traffic Control (ATC) system from a ground-based system to a satellite-based system. Such satellite-based systems are believed to introduce efficiencies in the air transportation system by enabling efficient flight paths previously unattainable in the industry.

SUMMARY

Embodiments of the present disclosure relate to Operational Flight Efficiency Evaluation (OFEE) system for an aircraft. The OFEE system comprises an Avionics Situation Awareness Device (ASAD). The ASAD includes one or more processors, a memory communicatively coupled to the one or more processors, and a flight data collection interface configured to, via the one or more processors, collect empirical flight data for a flight and store the empirical flight data in the memory. The OFEE further comprises a Simulation And Comparison System (SACS) in communication with the ASAD. The SACS includes a database communicatively coupled to a National Airspace System (NAS) and configured to automatically acquire and store avionic system configurations available for flight efficiencies from the NAS. The SACS also includes a simulator configured to identify at least one avionics upgrade based on the collected empirical flight data and the avionics systems available for flight efficiencies.

In one example embodiment, the flight data collection interface can be communicatively coupled to an aircraft recording system, wherein the aircraft recording system is configured to capture the aircraft's 2D-, 3D-, or 4D-flight trajectory positional information during the flight. In this example, the fourth dimension is time.

In another example embodiment, the collected empirical flight data can include at least one of: technological capabilities of the aircraft, registered flight plan of aircraft, actual flight path of aircraft, positional information of departure runway, positional information of arrival runway, nautical miles between each flight segment of the actual flight path, starting fuel amount, ending fuel amount, and environmental information related to the actual flight path, the environmental information including at least one of: weather and aircraft traffic during flight for each flight segment of the actual flight path.

In yet another example embodiment, the database can periodically send an inquiry to the NAS for potential updated avionics systems configurations and automatically acquires potential updated avionics systems configurations. In a further example embodiment, information associated with the avionics systems can include at least one of: instrument procedure information for an applicable volume of airspace, and avionics technologies that are fully operational and approved in the applicable airspace and at departure and arrival airports.

In an additional example embodiment, the simulator can be further configured to: compute total nautical air miles of: i) an actual flight path of the aircraft and ii) a registered flight path of the aircraft; compute a great-circle distance from the collected empirical flight data; identify at least one avionic system configuration available for the aircraft to achieve a flight path closely mapped to the great-circle distance and flown at optimized flight levels using both a no-wind model and a model using actual wind data from the registered flight path; and determine cost-savings for an operator of the aircraft based on the flight path closely mapping to the great-circle distance versus either i) the actual flight path of the aircraft or ii) the registered flight path of the aircraft.

BRIEF DESCRIPTION OF THE DRAWINGS

The foregoing and other objects, features and advantages will be apparent from the following more particular description of the embodiments, as illustrated in the accompanying drawings in which like reference characters refer to the same parts throughout the different views. The drawings are not necessarily to scale, emphasis instead being placed upon illustrating the principles of the embodiments.

DETAILED DESCRIPTION

Figure 1:
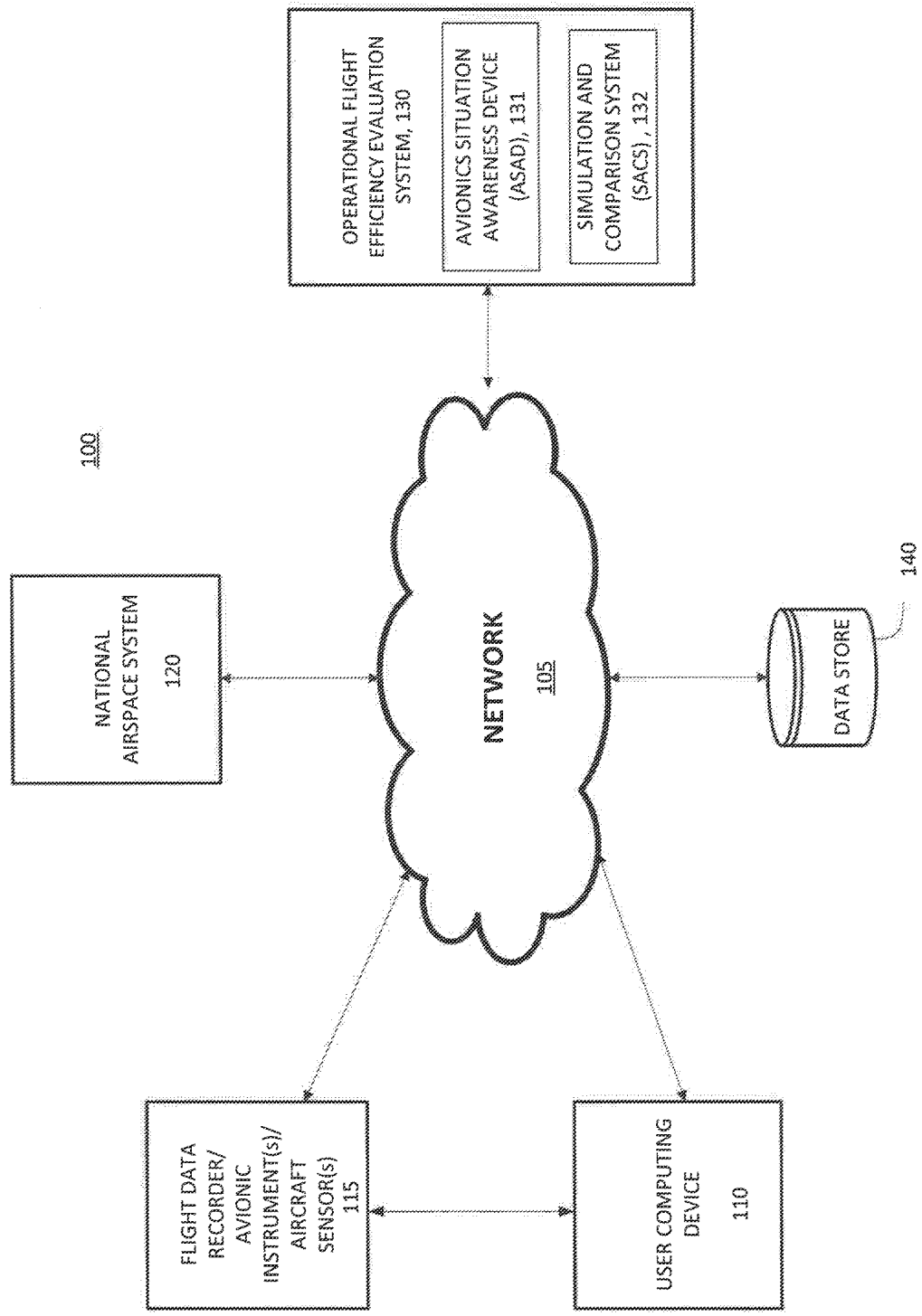
FIG. 1 is a schematic block diagram of a communications network for implementing an embodiment of the present disclosure.

A description of example embodiments of the present disclosure follows.

In the today's operating environment, a flight plan route is created using published navigation procedures and filed with Air Traffic Control (ATC). There are two phases of a flight plan: filed (registered) and cleared (authorized). Pilots/Operators file (or request) a particular routing prior to commencing a flight. The request is the flight plan on "file." The ATC then reviews the "plan" and assigns (or "clears") the pilot/operator the route & altitude that is expected to be complied with. Part of the clearance can be to maintain a heading until "intercepting" a published procedure (e.g., a Standard Instrument Departure (SID)). In sum, the pilot's flight plan will have a departure element, an en route portion, and an arrival plan. For the departure route the pilot will request a SID that proceeds in the direction of the destination. Then, the SID will have a transition point to an airway. Multiple airways can be used in the en route portion of the flight plan. Airways are constructed from Waypoints (latitude and longitude) and/or radio stations. Near the destination airport and approaching the top of the descent point, pilots will connect an airway with a Standard Terminal Arrival procedure (STAR). The STAR contains a ground track, speed, and altitude limit to align the aircraft with an Instrument Approach Procedure (IAP) and with the runway. The ATC system tries to allow operators to complete their flight plan as requested or assigns the best flight route possible based on a current demand of the system and capability of the aircraft.

However, as stated above, the FAA estimates that increasing congestion in the air transportation system of the United States, if unaddressed, will cost the American economy $22 billion annually in lost economic activity by 2022. In response to the concern of increasing congestion and lost economic activity, the government, along with industry leaders, is in the process of implementing a Next Generation Air Transportation System (NextGen) across the United States. The goal of NextGen is to transform America's ATC system from a ground-based system to a satellite-based system. NextGen systems include avionics that improve aircraft communication, surveillance, and navigation technologies. Accordingly, it is theorized that aircraft employing NextGen technologies can fly shorter and more efficient routes, thereby providing large cost-savings and reducing lost economic activity due to inefficiencies in the air transportation system.

A proxy for quantifying the efficiency of the air transportation system is examining the total distance traveled by an aircraft. The total distance traveled by an aircraft is a function of the route the aircraft travels from liftoff to touchdown. This route flown is directly influenced by the avionic technologies employed by the aircraft, and the route necessary to avoid obstacles, and terrain. The most efficient route an aircraft can take between departure and arrival locations is defined as a route that achieves a flight path having a distance closest to a great-circle distance between departure and arrival locations. The great-circle distance between the departure and arrival locations is, generally, a length of a direct parabolic line between the departure and arrival locations after terrain and obstacles have been cleared. However, due to technological limitations of many aircraft and ATC systems, such flight paths cannot be achieved. Accordingly, the current inefficiencies in the air transportation system can only be corrected if owners and operators of aircraft employ these new systems in their aircraft.

Although flight efficiencies can clearly be achieved, owner and operators of aircraft do not invest in new technologies without having a clear understanding of the potential Return On Investment (ROI) from acquiring and outfitting their aircraft with new avionic technologies. Accordingly, owner and operators of aircraft need a system that is able to gather flight data, simulate efficiencies using new avionic technologies, and attribute a financial value to those efficiencies.

Embodiments of the present disclosure relates to an OFEE system and method that measures operational benefits of upgrading aviation equipment. In some example embodiments, the OFEE system and method compares actual flight path history with a simulated flight path achievable using new avionic technologies. The OFEE system and method identifies a set of avionic technologies that would achieve a more efficient flight path with an economical benefit that would be of value to an owner and operator of an aircraft.

FIG. 1 is a schematic block diagram of a communications network 105 for implementing an embodiment of the present disclosure. The communications network 105 is depicted as a distributed computer environment 100. The communications network 105 includes a collection of communication links interconnecting a plurality of nodes, such as a user computing device 110, Flight Data Recorder 115, NAS 120, and OFEE system 130. The nodes can be interconnected via access points (not shown) and intermediate nodes (now shown) of the communications network 105. Those skilled in the art will appreciate that the network 105 may be any wired network, wireless network, or combination thereof. In addition, the network 105 may be a personal area network, local area network, wide area network, cable network, satellite network, cellular telephone network, or combination thereof. The interconnected nodes communicate with each other by, for example, exchanging data packets according to a pre-defined set of network protocols, such as the Transmission Control Protocol/Internet Protocol (TCP/IP) and the Session Initiation Protocol (SIP). A network protocol as used herein is a formal set of rules that define how data is exchanged between nodes in a communication network (e.g., the communication network 105 of FIG. 1).

The OFEE 130 includes an ASAD 131 and a SACS 132. The OFEE 130 may be embodied in a plurality of components, each operating an instance of the response OFEE. A server or other computing component implementing the OFEE 130 may include a network interface, memory, processing unit, and computer-readable medium drive, all of which may communicate with each other, for example, by way of a communication bus. The network interface may provide connectivity over the network 105 and/or other networks or computer systems. The processing unit may communicate to and from memory containing program instructions that the processing unit executes in order to operate the OFEE 130. The memory generally includes RAM, ROM, and/or other persistent and auxiliary memory.

The user computing device 110 may include any communication device, such as a PC, kiosk, thin client, home computer, and dedicated or embedded machine. Further examples may include laptop or tablet computers, personal computers, smart phones, Personal Digital Assistants (PDAs), hybrid PDAs/mobile phones, mobile phones, electronic book readers, set-top boxes, and the like.

The flight data recorder 115 may include an aircraft interface board, audio compressor board, memory interface cable, memory, and acquisition processor board. The flight data recorder 115 may also include a high-temperature insulation, armor (e.g., stainless steel armor), and an underwater locator beacon. The flight data recorder 115 may also include sensors such as altitude sensors, internal pressure sensors, and temperature sensors. The aircraft interface board may interface with aircraft sensors such as GPS, system controls (e.g., console, keyboards, and navigation), airspeed and altitude sensors, attitude gyro, radio altimeter, accelerometer rate gyros, and altimeters. Accordingly, the flight data recorder 115 is able to collect a comprehensive set of actual flight data for use to compare to an optimized, best-case profile. For example, systems that are used by the flight data recorder 115 include: Aircraft Heading and Reference Systems (AHRS) for attitude and heading; Air Data Computers (ADC) for pressure, temperature, speed, acceleration rate, etc.; Flight Management System (FMS) for interface with navigation systems (i.e. Global Navigation Satellite System (GNSS) and/or Inertial Reference Systems); Flight Director (FD) & Mode Control Panel (MCP) interface with Autopilot, Auto Throttle, and ground-based navigation sensors (VOR, LOC, ILS, NDB).

As stated above, the OFEE 130 includes ASAD 131. The ASAD 131 can include at least one processor communicatively coupled to at least one memory. Further, the ASAD includes a flight data collection interface that is configured to collect empirical flight data for a flight and store the flight data in memory (e.g., data store 140). In an example, the flight data collection interface may interface with the flight data recorder 115. In other examples, the flight data collection interface may interface with the flight data recorder 115 once the recorder 115 is communicatively coupled to network 105. In a further embodiment, the flight data collection device may indirectly retrieve the flight data via user computing device 110. The flight data that may be collected by the flight data collection interface can include at least one of: technological capabilities of the aircraft, registered flight plan of the aircraft, actual flight path of the aircraft, positional information of departure runway, positional information of arrival runway, nautical miles between each flight segment of the actual flight path, starting fuel amount, ending fuel amount, and environmental information related to the actual flight path. The environmental information including at least one of: weather and aircraft traffic during flight for each flight segment of the actual flight path.

It should be noted that the computer environment 100 could also operate within a computer system having a fewer or greater number of components than are illustrated in FIG. 1. Thus, the depiction of computer environment 100 should be taken as illustrative and not limiting of the present disclosure. For example, the environment 100 could implement various web services components (including but not limited to virtual utility computing services, a.k.a. "cloud computing services") and peer-to-peer network configurations to implement at least a portion of the processes described herein.

As illustrated by FIG. 1, a flight data recording device 115 is in communication with network 105. The flight data recording device 115 can include any device capable of capturing pre-flight data, in-flight data, and post-flight data of an aircraft. For example, the flight data recording device can include at least a flight transponder, avionic instrumentation, and aircraft sensors. Pre-flight data can include flight plan data, aircraft general technical and avionic information, pre-flight fuel, and pre-flight weight. During a flight, the flight data recording device 115, can capture in-flight data associated with, for example, fuel consumption, actual flight path flown, weather data, and air traffic information. In addition, the flight data recording device 115 can be configured to automatically record and capture GPS positional information of the aircraft during the flight. After a flight, the flight data recording device 115 can capture final weight, final fuel quantity and flight-time. In some embodiments, a user computing device 110 can be configured to be in communication with the flight data recording device to collect the captured data. The user computing device 110 can included data from an Electronic Flight Bag (EFB). An EFB is an electronic information management device like a hand-held tablet/laptop or a flight deck installed system like a Performance Data Computer (PDC). An EFB is a performance computing platform intended to reduce paper-based reference material and to host software to automate functions normally conducted by hand. EFBs can display performance calculations based on winds, alternate routes/altitudes, and speed. Results can be displayed in time, distance, and fuel burned.

As stated above, the OFEE 130 also includes the SACS 132. The SACS 132 includes a database (e.g., data store 140) that is communicatively coupled to the NAS 120. The database is configured to automatically acquire and store avionic system configurations available for flight efficiencies from the NAS. For example, the database can be configured to periodically send an inquiry to the NAS for updated avionics systems configuration information. In response to determining that updated information exists, the database acquires and stores the updated avionics systems information. The information associated with the avionics systems configurations includes at least: instrument procedure information for an applicable volume of airspace, and avionics technologies that are operational and approved in the applicable airspace and at departure and arrival airports.

Accordingly, the NAS 120 is an information hub for NextGen systems. In particular, the NAS 120 includes information associated with all the airspace from the surface of the earth up to an including 60,000 ft. mean sea level. The airspace is both controlled and uncontrolled airspace and consists of classes A, B, C, D, E and G.

Further, the SACS 132 includes a simulator to identify at least one avionics upgrade based on the collected empirical flight data and the avionics system configurations available for flight efficiencies. In an example, using the collected flight data, the simulator computes total nautical air miles of: i) an actual flight path of the aircraft and ii) a registered flight path of the aircraft. The simulator also computes a great-circle distance from the collected empirical flight data (e.g., the great-circle distance from the departing airstrip and landing airstrip). Further, the simulator identifies at least one avionic system configuration available for the aircraft to achieve a flight path closely mapped to the great-circle distance and flown at optimized flight levels using both a no-wind model and a model using actual wind data from the registered flight path.

The no-wind model uses the ground track and altitudes from the actual flight and compares it to the great-circle route. (The use of winds skews the data either positively or negatively). The wind model uses the empirical flight data and compares it to the parabolic great-circle route. The fuel burn and flight-time may be "wind-aided" thus the no-wind model is needed. The key performance data is total fuel burn (from takeoff to touchdown), flight-time (from engine start-up to engine shut-down), and total distance flown. The SACS tool 132 will compute three performance data points: fuel burn, total distance, and total flight-time (from engine start-up to engine shut-down). The baseline or "optimum" flight path distance is the great-circle route from the start of the departure (lat/long) runway to the touchdown point (lat/long) at the arrival runway. The fuel burn and time of flight (e.g., determined from long-range cruise data) can be obtained from the manufacture's Aircraft Flight Manual. The empirical performance data is captured by the User Computing Devise (110) and the FDR (115). The SACS 132 will compute no-wind performance data—derived from the actual flight (empirical data)—and compare both the no-wind and actual flight data to the baseline profile. The difference between the optimum and the no-wind model, plus any air miles needed to avoid terrain and/or obstacles is a measure of the inefficiency of the aircraft and/or the NAS. If the inefficiency is the result of aircraft equipage, then new avionics will decrease the delta. The magnitude of the delta is an opportunity to show a positive ROI using the OFEE. The FAA's aim is to improve the efficiency of the NAS with the NextGen program.

As stated herein, an owner/operator would most likely be motivated to employ updated avionics technologies if a clear ROI is obtained by the time/monetary investment associated with an upgrade. To that end, the simulator also determines a cost-savings for an operator of the aircraft based on the flight path closely mapping to the great-circle distance versus either i) the actual flight path of the aircraft or ii) the registered flight path of the aircraft. The cost-savings can be associated with an individual flight or over a plurality flights flown by the aircraft.

Figure 2:
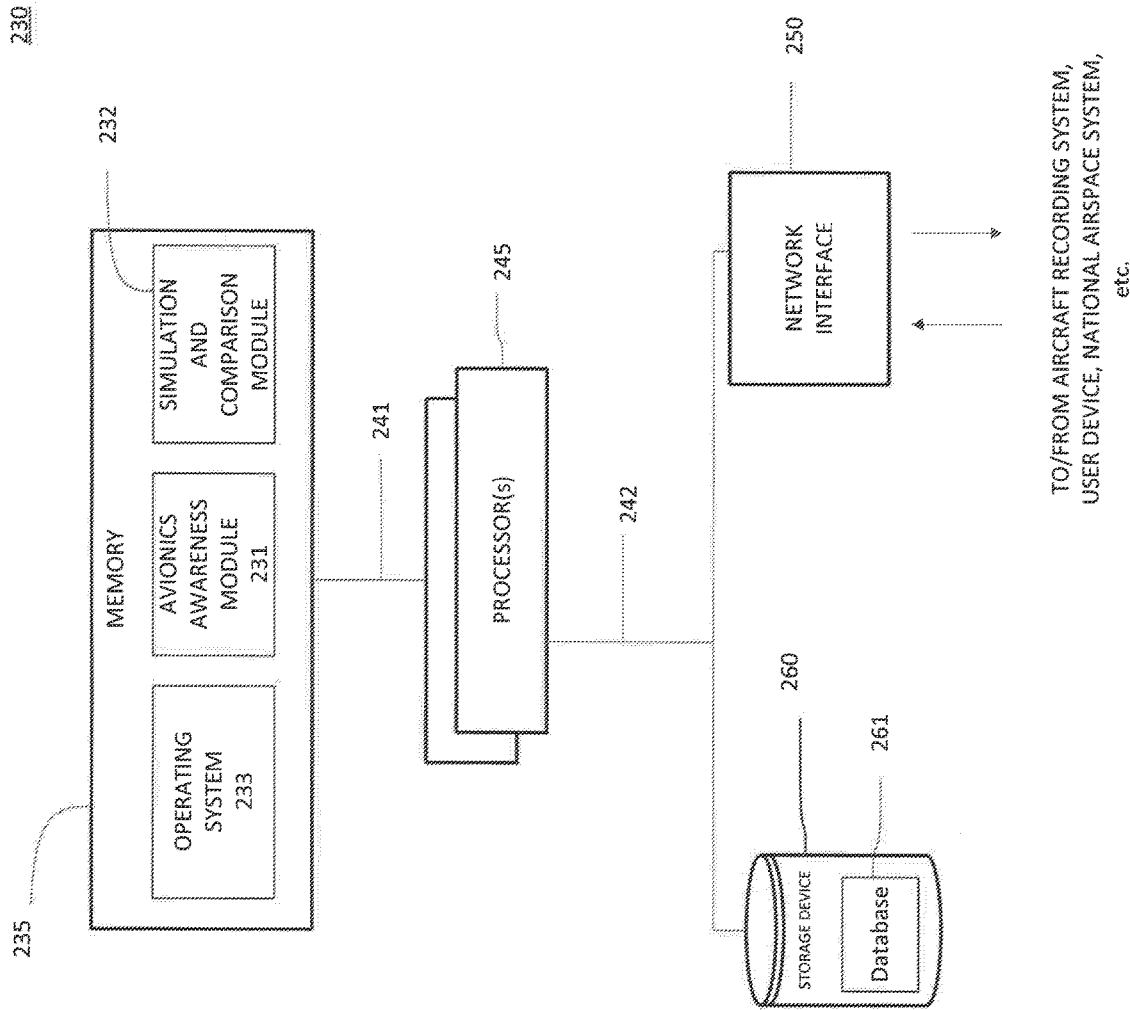
FIG. 2 is a block diagram of a processing system of an OFEE system, in accordance with an example embodiment of the present disclosure.

FIG. 2 is a block diagram of a processing system of an OFEE system 230, in accordance with an example embodiment of the present disclosure. The OFEE 230 includes a memory 235 coupled to processor(s) 245 via a memory bus 241, and a storage device 260 and an interface 250 coupled to the processor(s) 245 via an input/out (I/O) bus 242. It should be noted that the OFEE 230 may include other devices, such as keyboards, display units and the like. The interface 250 interfaces the OFEE 230 to devices (e.g., flight data recorder 115, user computing device 110, NAS 120 of FIG. 1) communicatively coupled to a network (e.g., the network 105 of FIG. 1). In addition, the interface 250 enables data (e.g., packets) to be transferred between the OFEE 230 and the devices. The network interface 250 may include conventional circuitry that incorporates signal, electrical and mechanical characteristics, and interchange circuits to interface with physical media of the user device and protocols running over that media. The storage device 260 is a storage device (e.g., a disk) structured to store, inter alia, flight data, aircraft data, and NextGen avionics information.

The memory 235 is an example computer-readable medium, optionally implemented as a RAM employing RAM devices, such as DRAM devices and/or flash memory devices. The memory 235 contains various software and data structures used by processor(s) 245 such as software and data structures used by the processor(s) 245, such as software and data structures that implement aspects of the present disclosure. Specifically, the memory 235 may store software configured to serve as an operating system 233 or provide avionics awareness module 231 and simulation and comparison module 232. The operating system 233 can be used to functionally organize the OFEE 230 by invoking operations in support of processes and services executing on the OFEE 230, such as the avionics awareness module 231 and the simulation and comparison module 232.

The storage device 260 may include a database 261, which may be implemented in the form of a data structure. The data structure is configured to hold information used by the OFEE 230 to determine flight efficiencies achievable using available avionic upgrades.

Figure 3:
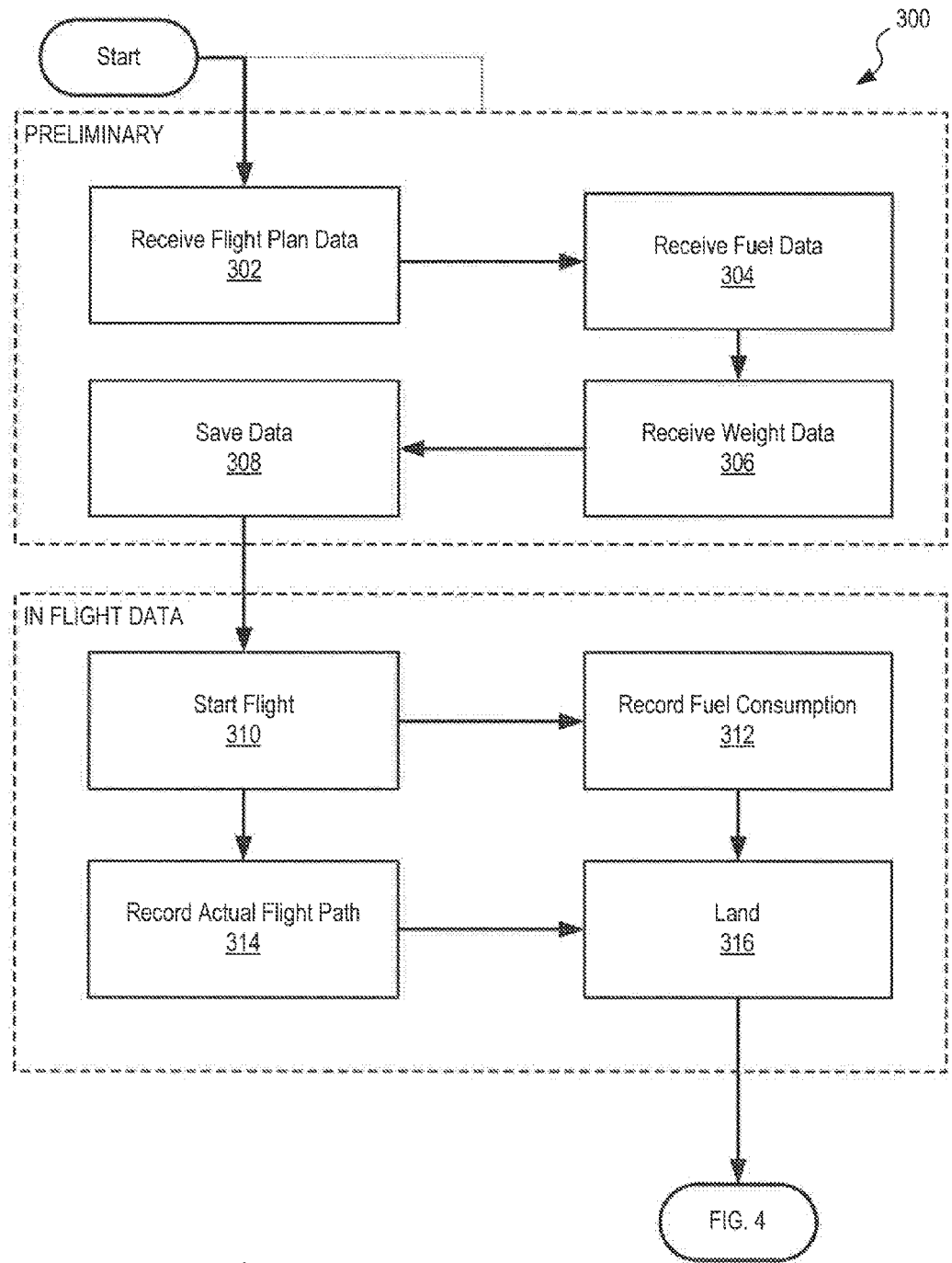
FIG. 3 is a flowchart that schematically illustrates preliminary and in-flight data collection methods for recording actual flight data, according to an embodiment of the present disclosure.

FIG. 3 is a flowchart that schematically illustrates preliminary and in-flight data collection methods 300 for recording actual flight data, according to an embodiment of the present disclosure. In an embodiment, an OFEE (e.g., the OFEE 130 of FIG. 1) system collects operator and vehicle execution information, including, but not limited to, aircraft performance and avionics equipage of a subject aircraft. Prior to a flight, the method 400, executed by the OFEE, includes, at 302, collecting the flight plan of a flight. In addition, the method 300, at 304, includes collecting fuel information (e.g., fuel levels and type/grade of fuel). The OFEE can interface with an aircraft's instrumentations to retrieve this information. Alternatively, the OFEE may be in communication with a user communication device (e.g., computing device 110 of FIG. 1) to obtain this data. Similarly, the method 300, at 306, collects weight information of the aircraft pre-departure (e.g., once the aircraft is fueled and fully loaded with, for example, passengers and associated baggage, etc.). At 308, the method 300 stores this information in a data store (e.g., data store 140 of FIG. 1).

During the flight, the method 300 includes collects the actual route data, assigned altitude data, and instrument procedures. For example, at 310, the method 300 records the start time of the flight and all positioning information associated with the start of the flight. This information can be collected by the flight data recording device (e.g., the flight data recorder 115 of FIG. 1). In addition, the method 300, at 312, records fuel consumption of the aircraft via an interface between the flight recording device and aircraft instrumentation. Further, the method 300, at 314, using, for example, a flight recorder, records the actual flight path traveled by the aircraft (in four dimensions). This can be accomplished by monitoring the GPS derived 4D positional information of the aircraft. The flight recorder continuously records the position of the aircraft. In alternative embodiments, the flight recorder of 314 may be programmed to periodically collect 4D positional information of the aircraft. The periodicity can be in set intervals or varied.

The method 300, at 416, records information associated with the landing of the aircraft. This information can include positional information of the aircraft, fuel amounts, weight, etc.

Figure 4:
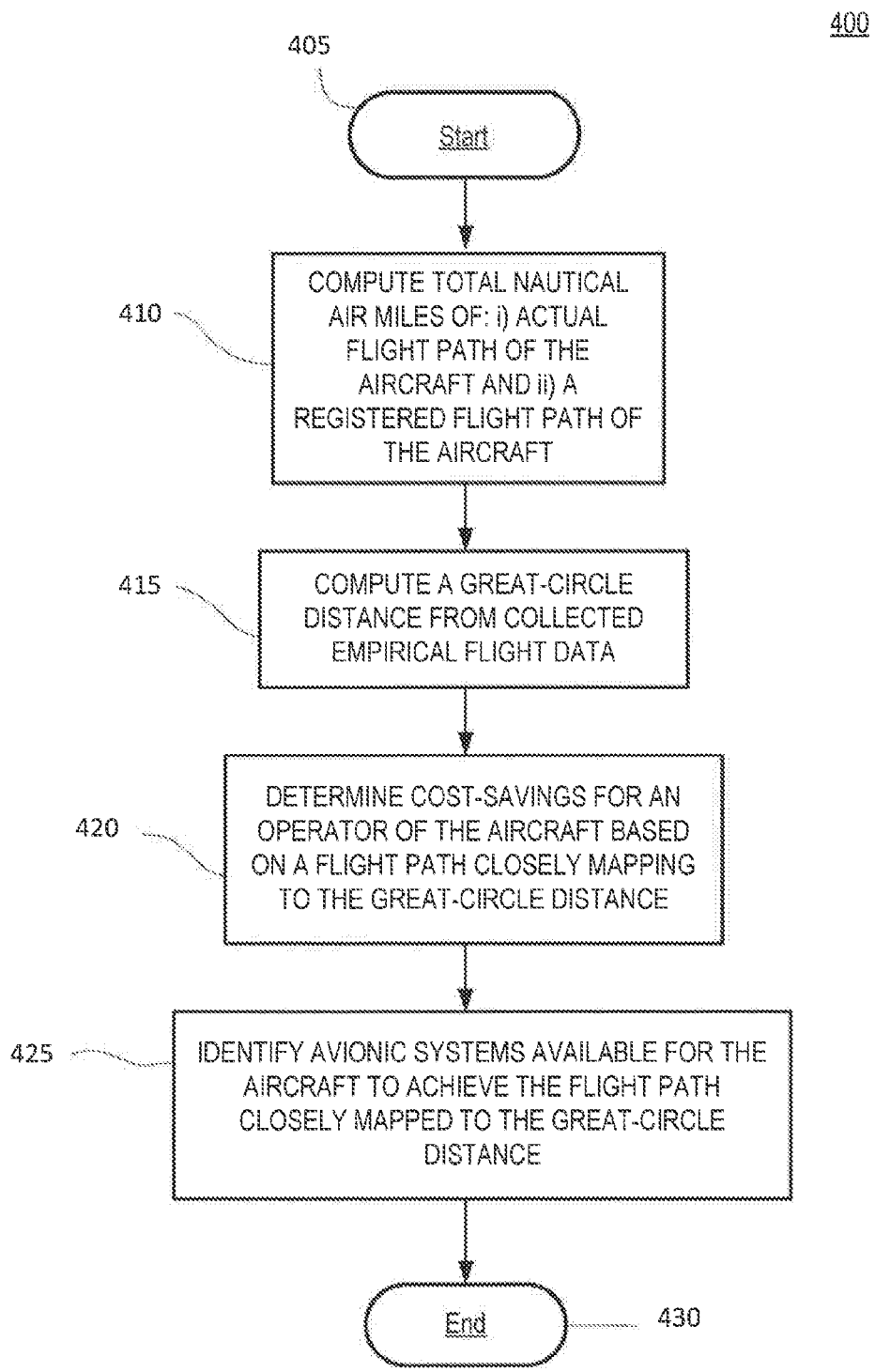
FIG. 4 is a flowchart that schematically illustrates generating the simulation of the recorded flight utilizing updated avionics for comparison to the recorded flight data and suggesting avionic upgrades, according to an embodiment.

Subsequent to the flight, the OFEE performs post-flight data analysis as illustrated by FIG. 4. FIG. 4 is a flowchart 400 that schematically illustrates generating the simulation of the recorded flight utilizing NextGen avionics for comparison to the recorded flight data and suggesting avionic upgrades, according to an embodiment. The method 400 begins at 405. At 410, the method 400 includes computing total nautical air miles of: i) the actual flight path of the aircraft and ii) the registered flight path of the aircraft. The method 400 uses the pre-flight, in-flight, and post-flight empirical data collected by the OFEE (e.g., the OFEE 130 of FIG. 1). At 415, the method computes a great-circle distance from the collected empirical data. As stated herein, the great-circle distance is, generally, a length of a direct parabolic line between the departure and arrival locations of the aircraft. The method, at 420, then determines a cost-savings for an operator of the aircraft based on a flight path closely mapping to the great-circle distance. Further, the method 400, at 425, identifies avionic systems available for the aircraft to achieve a flight path closely mapped to the great-circle distance. For example, the method 400, at steps 420-425, includes calculating the cost-savings based on both the actual flight path and the registered flight path. The cost-savings can include a Return On Investment metric that provides an operator a clear understanding of savings in relation to the cost/expenditure of acquiring and outfitting the aircraft with updated avionic systems. This metric enables an operator/owner of an aircraft to make a clear decision on whether or not to implement upgrades.

Figure 5A:
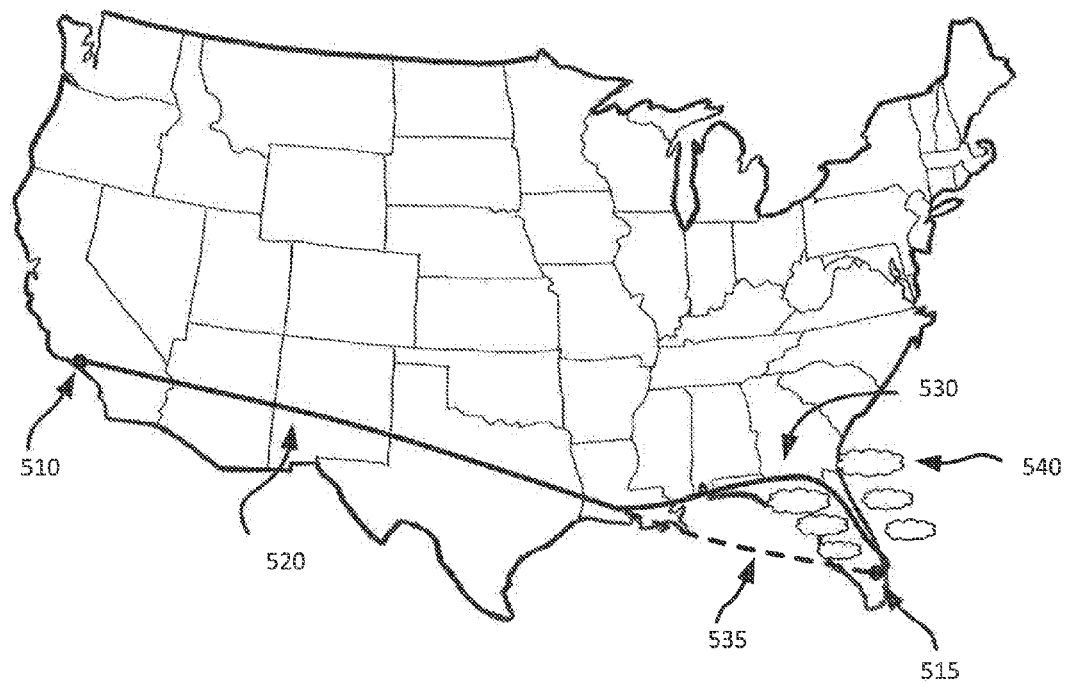
FIGS. 5A and 5B illustrate a comparison between an actual flight path and a projected flight path using updated avionic systems according to an embodiment of the present disclosure.
Figure 5B:
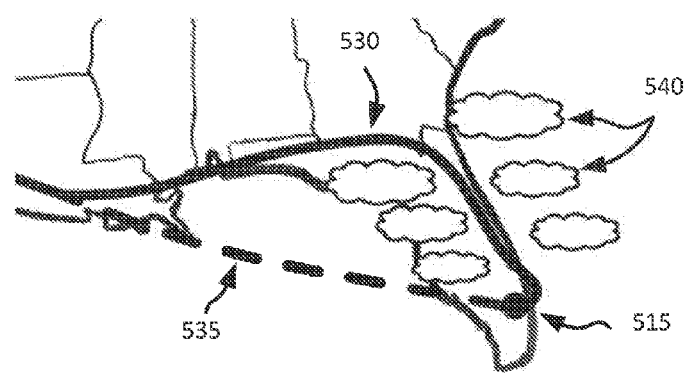

FIGS. 5A-B illustrate a comparison between an actual flight path and a projected flight path using updated avionic systems according to an embodiment of the present disclosure. As illustrated, a departure location 510 of an aircraft is from a city in southern California (e.g., Los Angeles). An arrival location 515 of the aircraft is a city in southern Florida (e.g., Miami). Using conventional avionic systems, an aircraft's flight path would consist of first segment 520 and second segment 530. The first segment 520 is reasonably direct. However, once the aircraft approached the Gulf of Mexico, existing avionic technologies require the aircraft to take more of a land-based trajectory. Accordingly, the aircraft deviates from a most direct route to a route defined by the second segment 530. The second segment 530, in this example, is further influenced by storm system 540 which is even longer than a more of a coastal approach which is easily visualized. As discussed herein, an OFEE system (e.g., the OFEE 130 of FIG. 1) would provide a recommended set of avionics that would enable the aircraft to achieve a flight path that consists of the first segment 520 and third segment 535. The OFEE would also provide cost-savings analysis would provide the owner/operator of the aircraft with measurable empirical data of a value of upgrading avionics.

Given the goal of the FAA to achieve nationwide flight efficiency, the OFEE of the present disclosure would advantageously assist in that endeavor.

The above described systems and methods can be implemented in digital electronic circuitry, in computer hardware, firmware, and/or software. The implementation can be as a computer program product. The implementation can, for example, be in a machine-readable storage device, for execution by, or to control the operation of, data processing apparatus. The implementation can, for example, be a programmable processor, a computer, and/or multiple computers.

A computer program can be written in any form of programming language, including compiled and/or interpreted languages, and the computer program can be deployed in any form, including as a stand-alone program or as a subroutine, element, and/or other unit suitable for use in a computing environment. A computer program can be deployed to be executed on one computer or on multiple computers at one site.

Method steps can be performed by one or more programmable processors executing a computer program to perform functions of the invention by operating on input data and generating output. Method steps can also be performed by and an apparatus can be implemented as special purpose logic circuitry. The circuitry can, for example, be a Field Programmable Gate Array (FPGA) and/or an Application-Specific Integrated Circuit (ASIC). Subroutines and software agents can refer to portions of the computer program, the processor, the special circuitry, software, and/or hardware that implement that functionality.

Processors suitable for the execution of a computer program include, by way of example, both general and special purpose microprocessors, and any one or more processors of any kind of digital computer. Generally, a processor receives instructions and data from a read-only memory or a random access memory or both. The essential elements of a computer are a processor for executing instructions and one or more memory devices for storing instructions and data. Generally, a computer can include, can be operatively coupled to receive data from and/or transfer data to one or more mass storage devices for storing data (e.g., magnetic, magneto-optical disks, or optical disks).

Data transmission and instructions can also occur over a communications network. Information carriers suitable for embodying computer program instructions and data include all forms of non-volatile memory, including by way of example semiconductor memory devices. The information carriers can, for example, be EPROM, EEPROM, flash memory devices, magnetic disks, internal hard disks, removable disks, magneto-optical disks, CD-ROM, and/or DVD-ROM disks. The processor and the memory can be supplemented by, and/or incorporated in special purpose logic circuitry.

To provide for interaction with a user, the above described techniques can be implemented on a computer having a display device. The display device can, for example, be a Cathode Ray Tube (CRT) and/or a Liquid Crystal Display (LCD) monitor. The interaction with a user can, for example, be a display of information to the user and a keyboard and a pointing device (e.g., a mouse or a trackball) by which the user can provide input to the computer (e.g., interact with a user interface element). Other kinds of devices can be used to provide for interaction with a user. Other devices can, for example, be feedback provided to the user in any form of sensory feedback (e.g., visual feedback, auditory feedback, or tactile feedback). Input from the user can, for example, be received in any form, including acoustic, speech, and/or tactile input.

The above described techniques can be implemented in a distributed computing system that includes a back-end component. The back-end component can, for example, be a data server, a middleware component, and/or an application server. The above described techniques can be implemented in a distributing computing system that includes a front-end component. The front-end component can, for example, be a client computer having a graphical user interface, a web browser through which a user can interact with an example implementation, and/or other graphical user interfaces for a transmitting device. The components of the system can be interconnected by any form or medium of digital data communication (e.g., a communication network). Examples of communication networks include a Local Area Network (LAN), a Wide Area Network (WAN), the Internet, wired networks, and/or wireless networks.

The system can include clients and servers. A client and a server are generally remote from each other and typically interact through a communication network. The relationship of client and server arises by virtue of computer programs running on the respective computers and having a client-server relationship to each other.

Packet-based networks can include, for example, the Internet, a carrier Internet Protocol (IP) network (e.g., Local Area Network (LAN), WAN, Aeronautical Mobile Airport Communications System (AeroMACS), Campus Area Network (CAN), Metropolitan Area Network (MAN), Home Area Network (HAN)), a private IP network, an IP Private Branch Exchange (IPBX), a wireless network (e.g., radio access network (RAN), 802.11 network, 802.16 network, General Packet Radio Service (GPRS) network, Hiper-LAN), and/or other packet-based networks. Circuit-based networks can include, for example, the Public Switched Telephone Network (PSTN), a Private Branch Exchange (PBX), a wireless network (e.g., RAN, bluetooth, Code-Division Multiple Access (CDMA) network, Time Division Multiple Access (TDMA) network, Global System For Mobile Communications (GSM) network), and/or other circuit-based networks.

The transmitting device can include, for example, a computer, a computer with a browser device, a telephone, an IP phone, a mobile device (e.g., cellular phone, PDA device, laptop computer, electronic mail device), and/or other communication devices. The browser device includes, for example, a computer (e.g., desktop computer, tablet, laptop computer) with a world wide web browser (e.g., Microsoft® Internet Explorer® available from Microsoft Corporation, Mozilla® Firefox available from Mozilla Corporation). The mobile computing device includes, for example, a Smartphone.

Comprise, include, and/or plural forms of each are open ended and include the listed parts and can include additional parts that are not listed. And/or is open ended and includes one or more of the listed parts and combinations of the listed parts.

One skilled in the art will realize the present disclosure may be embodied in other specific forms without departing from the spirit or essential characteristics thereof. The foregoing embodiments are therefore to be considered in all respects illustrative rather than limiting of the present disclosure described herein. Scope of the present disclosure is thus indicated by the appended claims, rather than by the foregoing description, and all changes that come within the meaning and range of equivalency of the claims are therefore intended to be embraced therein.

What is claimed is:

1. An Operational Flight Efficiency Evaluation (OFEE) system for an aircraft, the system comprising:
   an Avionics Situation Awareness Device (ASAD), the ASAD including:
      one or more processors,
      a memory communicatively coupled to the one or more processors,
      a flight data collection interface configured to, via the one or more processors, collect empirical flight data for a flight and store the empirical flight data in the memory; and
   a Simulation And Comparison System (SACS) in communication with the ASAD, the SACS including:
      a database communicatively coupled to a National Airspace System (NAS) and configured to automatically acquire and store avionic system configurations available for flight efficiencies from the NAS,
      a simulator configured to identify any possible avionics upgrade based on the collected empirical flight data and the avionics systems available for flight efficiencies.

2. The system of claim 1 wherein the flight data collection interface is communicatively coupled to an aircraft recording system, wherein the aircraft recording system is configured to automatically record and capture GPS positional information of the aircraft during the flight.

3. The system of claim 1 wherein the collected empirical flight data includes at least one of: technological capabilities of the aircraft, registered flight plan of aircraft, actual flight path of aircraft, positional information of departure runway, positional information of arrival runway, nautical miles between each flight segment of the actual flight path, starting fuel amount, ending fuel amount, and environmental information related to the actual flight path, the environmental information including at least one of: weather and aircraft traffic during flight for each flight segment of the actual flight path.

4. The system of claim 1 wherein the database periodically sends an inquiry to the NAS for updated avionics system configuration information and automatically acquires updated avionics systems information.

5. The system of claim 1 wherein information associated with the avionics systems includes at least one of: instrument procedure information for an applicable volume of airspace, and avionics technologies that are operational and approved in the applicable airspace and at departure and arrival airports.

6. The system of claim 1 wherein the simulator is further configured to:
   compute total nautical air miles of: i) an actual flight path of the aircraft and ii) a registered flight path of the aircraft;
   compute a great-circle distance from the collected empirical flight data;
   identify at least one avionic system available for the aircraft to achieve a flight path closely mapped to the great-circle distance and flown at optimized flight levels using both a no-wind model and a model using actual wind data from the registered flight path; and
   determine cost-savings for an operator of the aircraft based on the flight path closely mapping to the great-circle distance versus either i) the actual flight path of the aircraft or ii) the registered flight path of the aircraft.

7. The system of claim 6 wherein the similar determined the cost-savings by calculating a total flight-time, total distance, and fuel burn of the aircraft, wherein the total flight-time is calculated from engine start-up to engine shut-down of the aircraft.

8. The system of claim 6 wherein the simulator is further configured to determine a cost-savings for the operator over a plurality of flight paths flown by the aircraft.

* * * * *